US010850089B2

(12) United States Patent
Grant et al.

(10) Patent No.: US 10,850,089 B2
(45) Date of Patent: Dec. 1, 2020

(54) FLEXIBLE TUBING OCCLUSION ASSEMBLY

(71) Applicant: DEKA Products Limited Partnership, Manchester, NH (US)

(72) Inventors: Kevin L. Grant, Litchfield, NH (US);
Brett A. Rudolf, Hooksett, NH (US);
James D. Dale, Nashua, NH (US);
Jesse T. Bodwell, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 247 days.

(21) Appl. No.: 15/637,738

(22) Filed: Jun. 29, 2017

(65) Prior Publication Data

US 2017/0296803 A1 Oct. 19, 2017

Related U.S. Application Data

(62) Division of application No. 15/181,234, filed on Jun. 13, 2016, now Pat. No. 9,700,711, which is a division
(Continued)

(51) Int. Cl.
*A61M 39/28* (2006.01)
*A61M 1/36* (2006.01)
*F16K 7/06* (2006.01)

(52) U.S. Cl.
CPC ........ *A61M 39/284* (2013.01); *A61M 1/3638* (2014.02); *F16K 7/06* (2013.01)

(58) Field of Classification Search
CPC .............. A61M 5/142; A61M 5/14232; A61M 5/16881; A61M 2005/14208;
(Continued)

(56) References Cited

U.S. PATENT DOCUMENTS 350,850 A 10/1886 Tatum
2,816,514 A 12/1957 Freese
(Continued)

FOREIGN PATENT DOCUMENTS

EP 0815882 A2 1/1998
JP H03-162866 A 7/1991
(Continued)

OTHER PUBLICATIONS

Office Action for U.S. Appl. No. 09/357,645, filed Jul. 20, 1999, which Office Action is dated Jun. 23, 2000, and claims as pending for U.S. Appl. No. 09/357,645 as of Jun. 23, 2000.
(Continued)

*Primary Examiner* — Kami A Bosworth
(74) *Attorney, Agent, or Firm* — Wolf, Greenfield & Sacks, P.C.

(57) ABSTRACT

An occlusion assembly for compressing a pair of collapsible tubes comprises a frame comprising a tubing guide configured for positioning the collapsible tube. The occlusion assembly also comprises a tubing occluder mounted to the frame with an occluding member constructed and positioned to controllably occlude or release occlusion of the collapsible tube. A door mounted to the frame is positioned to cover at least a portion of the collapsible tube and tubing occluder when closed and provide user access when open. The assembly includes a retainer mechanism engaged by the door when the door is closed to permit operation of the tubing occluder when the door is closed and retain the tubing occluder in a non-occluding configuration when the door is opened.

21 Claims, 12 Drawing Sheets

Related U.S. Application Data of application No. 13/480,236, filed on May 24, 2012, now Pat. No. 9,364,655.

(58) Field of Classification Search
CPC ...... A61M 39/28–288; F16K 7/02–045; F16K 7/06; F16K 7/061; F16K 7/063–068; F16K 7/07; F16K 7/075; F16K 7/08
See application file for complete search history.

(56) References Cited

U.S. PATENT DOCUMENTS

| | | | |
|---|---|---|---|
| 2,985,192 A | 5/1961 | Taylor et al. | |
| 3,111,125 A | 11/1963 | Schulte et al. | |
| 3,335,753 A | 8/1967 | Kiser | |
| 3,411,534 A | 11/1968 | Rose | |
| 3,539,081 A | 11/1970 | Norton et al. | |
| 3,568,214 A | 3/1971 | Goldschmied et al. | |
| 3,575,161 A | 4/1971 | London | |
| 3,759,483 A | 9/1973 | Baxter | |
| 3,827,561 A | 8/1974 | Serfass et al. | |
| 3,918,490 A | 11/1975 | Goda | |
| 3,985,134 A | 10/1976 | Lissot et al. | |
| 3,991,972 A | 11/1976 | Eaton | |
| 4,061,142 A | 12/1977 | Tuttle | |
| 4,096,211 A | 6/1978 | Rameau | |
| 4,161,264 A | 7/1979 | Malmgren et al. | |
| 4,259,985 A | 4/1981 | Bergmann | |
| 4,322,054 A | 3/1982 | Campbell | |
| 4,398,908 A | 8/1983 | Siposs | |
| 4,425,116 A * | 1/1984 | Bilstad | A61M 39/285 137/595 |
| 4,428,745 A * | 1/1984 | Williams | A61M 39/28 137/883 |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,484,599 A | 11/1984 | Hanover et al. | |
| 4,501,405 A | 2/1985 | Usry | |
| 4,575,007 A | 3/1986 | Groth et al. | |
| 4,585,442 A | 4/1986 | Mannes | |
| 4,594,058 A | 6/1986 | Fischell | |
| 4,623,450 A | 11/1986 | Vantard et al. | |
| 4,643,710 A | 2/1987 | Troutner | |
| 4,645,489 A | 2/1987 | Krumme et al. | |
| 4,725,269 A | 2/1988 | Danby et al. | |
| 4,778,451 A | 10/1988 | Kamen | |
| 4,808,161 A | 2/1989 | Kamen | |
| 4,826,482 A | 5/1989 | Kamen | |
| 4,828,543 A | 5/1989 | Weiss et al. | |
| 4,833,329 A | 5/1989 | Quint et al. | |
| 4,878,646 A | 11/1989 | Edelman et al. | |
| 4,969,486 A | 11/1990 | Puzio | |
| 4,976,162 A | 12/1990 | Kamen | |
| 5,002,471 A | 3/1991 | Perlov | |
| 5,088,515 A | 2/1992 | Kamen | |
| 5,105,981 A | 4/1992 | Gehman | |
| 5,113,906 A | 5/1992 | Hogner | |
| 5,178,182 A | 1/1993 | Kamen | |
| 5,257,978 A * | 11/1993 | Haber | A61M 39/281 251/9 |
| 5,290,239 A * | 3/1994 | Classey | A61M 39/287 128/DIG. 12 |
| 5,300,044 A | 4/1994 | Classey et al. | |
| 5,318,414 A | 6/1994 | Lundback | |
| 5,328,487 A | 7/1994 | Starchevich | |
| D350,823 S | 9/1994 | Lanigan | |
| 5,350,357 A | 9/1994 | Kamen et al. | |
| 5,351,686 A | 10/1994 | Steuer et al. | |
| 5,411,472 A | 5/1995 | Steg, Jr. et al. | |
| 5,413,566 A | 5/1995 | Sevrain et al. | |
| 5,421,823 A | 6/1995 | Kamen et al. | |
| 5,423,738 A | 6/1995 | Robinson et al. | |
| 5,429,485 A | 7/1995 | Dodge | |
| 5,431,626 A | 7/1995 | Bryant et al. | |
| 5,437,635 A * | 8/1995 | Fields | A61M 5/16813 604/65 |
| 5,438,510 A | 8/1995 | Bryant et al. | |
| 5,441,231 A | 8/1995 | Payne et al. | |
| 5,472,325 A | 12/1995 | Svendsen | |
| 5,474,683 A | 12/1995 | Bryant et al. | |
| 5,575,310 A | 11/1996 | Kamen et al. | |
| 5,578,012 A | 11/1996 | Kamen et al. | |
| 5,628,908 A | 5/1997 | Kamen et al. | |
| 5,634,896 A | 6/1997 | Bryant et al. | |
| 5,692,729 A | 12/1997 | Harhen | |
| 5,901,745 A | 5/1999 | Buchtel | |
| 5,931,648 A | 8/1999 | Del Canizo | |
| 5,938,634 A | 8/1999 | Packard | |
| 5,989,423 A | 11/1999 | Kamen et al. | |
| 6,041,801 A | 3/2000 | Gray et al. | |
| 6,105,416 A | 8/2000 | Nelson et al. | |
| 6,223,130 B1 | 4/2001 | Gray et al. | |
| 6,261,262 B1 | 7/2001 | Briggs et al. | |
| 6,270,673 B1 | 8/2001 | Belt et al. | |
| 6,302,653 B1 | 10/2001 | Bryant et al. | |
| 6,382,923 B1 | 5/2002 | Gray | |
| 6,416,293 B1 | 7/2002 | Bouchard et al. | |
| 6,485,263 B1 | 11/2002 | Bryant et al. | |
| 6,595,948 B2 | 7/2003 | Suzuki et al. | |
| 6,604,908 B1 | 8/2003 | Bryant et al. | |
| 6,663,359 B2 | 12/2003 | Gray | |
| 6,722,865 B2 | 4/2004 | Domroese | |
| 6,749,403 B2 | 6/2004 | Bryant et al. | |
| 6,808,369 B2 | 10/2004 | Gray et al. | |
| 6,877,713 B1 | 4/2005 | Gray et al. | |
| 6,905,479 B1 | 6/2005 | Bouchard et al. | |
| 6,949,079 B1 | 9/2005 | Westberg et al. | |
| 7,124,996 B2 | 10/2006 | Clarke et al. | |
| 7,469,874 B2 | 12/2008 | Akahori | |
| 7,559,524 B2 | 7/2009 | Gray et al. | |
| 7,632,080 B2 | 12/2009 | Tracey et al. | |
| 7,662,139 B2 | 2/2010 | Demers et al. | |
| 7,766,301 B2 | 8/2010 | Gray et al. | |
| 7,776,006 B2 | 8/2010 | Childers et al. | |
| 7,794,141 B2 | 9/2010 | Perry et al. | |
| 7,967,022 B2 | 6/2011 | Grant et al. | |
| 8,042,563 B2 | 10/2011 | Wilt et al. | |
| 8,246,826 B2 | 8/2012 | Wilt et al. | |
| 8,273,049 B2 | 9/2012 | Demers et al. | |
| 8,292,594 B2 | 10/2012 | Tracey et al. | |
| 8,317,492 B2 | 11/2012 | Demers et al. | |
| 8,357,298 B2 | 1/2013 | Demers et al. | |
| 8,393,690 B2 | 3/2013 | Grant et al. | |
| 8,409,441 B2 | 4/2013 | Wilt | |
| 8,425,471 B2 | 4/2013 | Grant et al. | |
| 8,459,292 B2 | 6/2013 | Wilt et al. | |
| 8,491,184 B2 | 7/2013 | Kamen et al. | |
| 8,499,780 B2 | 8/2013 | Wilt et al. | |
| 8,545,698 B2 | 10/2013 | Wilt et al. | |
| 8,562,834 B2 | 10/2013 | Kamen et al. | |
| 8,721,879 B2 | 5/2014 | Van der Merwe et al. | |
| 8,721,884 B2 | 5/2014 | Wilt et al. | |
| 8,771,508 B2 | 7/2014 | Grant et al. | |
| 8,858,787 B2 | 10/2014 | Muller et al. | |
| 8,863,772 B2 | 10/2014 | Dale et al. | |
| 8,870,549 B2 | 10/2014 | Tracey et al. | |
| 8,888,470 B2 | 11/2014 | Demers et al. | |
| 8,926,294 B2 | 1/2015 | Demers et al. | |
| 8,968,232 B2 | 3/2015 | Kamen et al. | |
| 8,985,133 B2 | 3/2015 | Grant et al. | |
| 8,992,075 B2 | 3/2015 | Kamen et al. | |
| 8,992,189 B2 | 3/2015 | Wilt et al. | |
| 9,028,440 B2 | 5/2015 | Helmore et al. | |
| 9,028,691 B2 | 5/2015 | Grant et al. | |
| 9,115,708 B2 | 8/2015 | van der Merwe et al. | |
| 9,121,403 B2 | 9/2015 | Lanigan et al. | |
| 9,272,082 B2 | 3/2016 | Demers et al. | |
| 9,302,037 B2 | 4/2016 | Wilt et al. | |
| 9,364,655 B2 | 6/2016 | Grant et al. | |
| 9,517,295 B2 | 12/2016 | Wilt et al. | |
| 9,535,021 B2 | 1/2017 | Kamen et al. | |
| 9,539,379 B2 | 1/2017 | Grant et al. | |
| 9,550,018 B2 | 1/2017 | Demers et al. | |

(56) References Cited

U.S. PATENT DOCUMENTS

| | | |
|---|---|---|
| 9,555,179 B2 | 1/2017 | Wilt et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |
| 9,717,834 B2 | 8/2017 | Wilt et al. |
| 9,724,458 B2 | 8/2017 | Grant et al. |
| 9,795,728 B2 | 10/2017 | Grant et al. |
| 9,839,776 B2 | 12/2017 | Helmore et al. |
| 9,951,768 B2 | 4/2018 | Grant et al. |
| 9,987,407 B2 | 6/2018 | Grant et al. |
| 9,999,717 B2 | 6/2018 | Van der Merwe et al. |
| 10,077,766 B2 | 9/2018 | Demers et al. |
| 10,098,998 B2 | 10/2018 | Wilt |
| 10,201,650 B2 | 2/2019 | Wilt et al. |
| 10,302,075 B2 | 5/2019 | Tracey et al. |
| 2003/0181866 A1* | 9/2003 | Abrahamson ..... A61M 5/14228 604/250 |
| 2004/0091374 A1 | 5/2004 | Gray |
| 2005/0069425 A1 | 3/2005 | Gray et al. |
| 2005/0094485 A1 | 5/2005 | Demers et al. |
| 2005/0095141 A1 | 5/2005 | Lanigan et al. |
| 2005/0095152 A1 | 5/2005 | Dale |
| 2005/0095154 A1 | 5/2005 | Tracey et al. |
| 2005/0256447 A1 | 11/2005 | Richardson et al. |
| 2008/0015493 A1 | 1/2008 | Childers et al. |
| 2008/0058697 A1 | 3/2008 | Kamen et al. |
| 2008/0175719 A1 | 7/2008 | Tracey et al. |
| 2008/0208103 A1 | 8/2008 | Demers et al. |
| 2008/0216898 A1 | 9/2008 | Grant et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2008/0287854 A1 | 11/2008 | Sun |
| 2009/0004033 A1 | 1/2009 | Demers et al. |
| 2009/0008331 A1 | 1/2009 | Wilt et al. |
| 2009/0012448 A1 | 1/2009 | Childers et al. |
| 2009/0012449 A1 | 1/2009 | Lee et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012461 A1 | 1/2009 | Childers et al. |
| 2009/0043253 A1 | 2/2009 | Podaima |
| 2009/0076433 A1 | 3/2009 | Folden et al. |
| 2009/0088675 A1 | 4/2009 | Kelly et al. |
| 2009/0095679 A1 | 4/2009 | Demers et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0114582 A1 | 5/2009 | Grant et al. |
| 2009/0202367 A1 | 8/2009 | Gray et al. |
| 2010/0051529 A1 | 3/2010 | Grant et al. |
| 2010/0051551 A1 | 3/2010 | Grant et al. |
| 2010/0056975 A1 | 3/2010 | Dale et al. |
| 2010/0057016 A1 | 3/2010 | Dale et al. |
| 2010/0168682 A1 | 7/2010 | Braga et al. |
| 2010/0192686 A1 | 8/2010 | Kamen et al. |
| 2011/0098635 A1 | 4/2011 | Helmore et al. |
| 2011/0105877 A1 | 5/2011 | Wilt et al. |
| 2011/0218600 A1 | 9/2011 | Kamen et al. |
| 2011/0299358 A1 | 12/2011 | Wilt et al. |
| 2012/0035581 A1* | 2/2012 | Travis ................. A61M 39/28 604/500 |
| 2012/0106289 A1 | 5/2012 | Wilt et al. |
| 2012/0207627 A1 | 8/2012 | Demers et al. |
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0118619 A1 | 5/2013 | Loth et al. |
| 2013/0126413 A1 | 5/2013 | van der Merwe et al. |
| 2013/0177457 A1 | 7/2013 | Demers et al. |
| 2013/0284648 A1 | 10/2013 | Grant et al. |
| 2013/0304020 A1 | 11/2013 | Wilt et al. |
| 2014/0102299 A1 | 4/2014 | Wilt et al. |
| 2014/0102958 A1 | 4/2014 | Kamen et al. |
| 2014/0102970 A1 | 4/2014 | Wilt et al. |
| 2014/0112828 A1 | 4/2014 | Grant et al. |
| 2014/0153356 A1 | 6/2014 | Giant et al. |
| 2014/0199193 A1 | 7/2014 | Wilt et al. |
| 2014/0299544 A1 | 10/2014 | Wilt et al. |
| 2014/0309611 A1 | 10/2014 | Wilt et al. |
| 2014/0319041 A1 | 10/2014 | Wilt et al. |
| 2014/0322053 A1 | 10/2014 | van der Merwe et al. |
| 2015/0042366 A1 | 2/2015 | Wilt et al. |
| 2015/0050166 A1 | 2/2015 | Tracey et al. |
| 2015/0057603 A1 | 2/2015 | Helmore et al. |
| 2015/0125319 A1 | 5/2015 | Demers et al. |
| 2015/0196698 A1 | 7/2015 | Grant et al. |
| 2015/0196699 A9 | 7/2015 | Wilt et al. |
| 2015/0204807 A1 | 7/2015 | Kamen et al. |
| 2015/0224242 A1 | 8/2015 | Grant et al. |
| 2015/0265760 A1 | 9/2015 | Wilt et al. |
| 2016/0030658 A1 | 2/2016 | Van der Merwe et al. |
| 2016/0058933 A1 | 3/2016 | Ballantyne et al. |
| 2016/0175505 A1 | 6/2016 | Demers et al. |
| 2016/0175506 A1 | 6/2016 | Wilt et al. |
| 2016/0287859 A1 | 10/2016 | Grant et al. |
| 2017/0000938 A1 | 1/2017 | Wilt et al. |
| 2017/0100533 A1 | 4/2017 | Wilt et al. |
| 2017/0130705 A1 | 5/2017 | Demers et al. |
| 2017/0143886 A1 | 5/2017 | Wilt et al. |
| 2017/0241926 A1 | 8/2017 | Kamen et al. |
| 2017/0319765 A1 | 11/2017 | Wilt et al. |
| 2017/0326282 A1 | 11/2017 | Wilt et al. |
| 2017/0342972 A1 | 11/2017 | Wilt et al. |
| 2017/0368252 A1 | 12/2017 | Grant et al. |
| 2018/0055984 A1 | 3/2018 | Grant et al. |
| 2018/0296746 A1 | 10/2018 | van der Merwe et al. |
| 2018/0339094 A1 | 11/2018 | Grant et al. |
| 2018/0372084 A1 | 12/2018 | Grant et al. |
| 2019/0094163 A1 | 3/2019 | Kamen et al. |
| 2019/0160220 A1 | 5/2019 | Wilt et al. |

FOREIGN PATENT DOCUMENTS

| | | |
|---|---|---|
| JP | H03-118754 U | 12/1991 |
| JP | 2003-000704 A | 1/2003 |
| WO | WO 96/40320 A1 | 12/1996 |
| WO | WO 2009/094179 A2 | 7/2009 |
| WO | WO 2010/027435 A1 | 3/2010 |
| WO | WO 2012/162515 A2 | 11/2012 |

OTHER PUBLICATIONS

Office Action for U.S. Appl. No. 09/357,645, filed Jul. 20, 1999, which Office Action is dated Jan. 16, 2001, and claims as pending for U.S. Appl. No. 09/357,645 as of Jan. 16, 2001.

Office Action for U.S. Appl. No. 09/357,645, filed Jul. 20, 1999, which Office Action is dated May 17, 2002, and claims as pending for U.S. Appl. No. 09/357,645 as of May 17, 2002.

Examiner's Answer to Appeal Brief for U.S. Appl. No. 09/357,645, filed Jul. 20, 1999, which Answer is dated Feb. 25, 2003, and claims as pending for U.S. Appl. No. 09/357,645 as of Feb. 25, 2003.

BPAI Decision on Appeal for U.S. Appl. No. 09/357,645, filed Jul. 20, 1999, which Decision is dated Jan. 30, 2004, and claims as pending for U.S. Appl. No. 09/357,645 as of Jan. 30, 2004.

Office Action for U.S. Appl. No. 10/951,441, filed Sep. 28, 2004, published as US 2005-0069425 on Mar. 31, 2005 which Office Action is dated Sep. 1, 2005, and claims as pending for U.S. Appl. No. 10/951,441 as of Sep. 1, 2005.

(56) References Cited

OTHER PUBLICATIONS

Office Action for U.S. Appl. No. 10/951,441, filed Sep. 28, 2004, published as US 2005-0069425 on Mar. 31, 2005 which Office Action is dated May 5, 2006, and claims as pending for U.S. Appl. No. 10/951,441 as of May 5, 2006.
Office Action for U.S. Appl. No. 10/951,441, filed Sep. 28, 2004, published as US 2005-0069425 on Mar. 31, 2005 which Office Action is dated Dec. 4, 2007 and claims as pending for U.S. Appl. No. 10/951,441 as of Dec. 4, 2007.
Office Action for U.S. Appl. No. 10/951,441, filed Sep. 28, 2004, published as US 2005-0069425 on Mar. 31, 2005 which Office Action is dated Aug. 20, 2008, and claims as pending for U.S. Appl. No. 10/951,441 as of Aug. 20, 2008.
Office Action for U.S. Appl. No. 12/423,665, filed Apr. 14, 2009, published as US 2009-0202367 on Aug. 13, 2009 which Office Action is dated Jun. 26, 2009, and claims as pending for U.S. Appl. No. 12/423,665 as of Jun. 26, 2009.
Office Action for U.S. Appl. No. 12/198,947, filed Aug. 27, 2008, published as US 2010-0057016 on Mar. 4, 2010, which Office Action is dated Oct. 15, 2009, and claims as pending for U.S. Appl. No. 12/198,947 as of Oct. 15, 2009.
Office Action for U.S. Appl. No. 12/198,947, filed Aug. 27, 2008, published as US 2010-0057016 on Mar. 4, 2010, which Office Action is dated Jul. 14, 2010, and claims as pending for U.S. Appl. No. 12/198,947 as of Jul. 14, 2010.
Office Action for U.S. Appl. No. 12/198,947, filed Aug. 27, 2008, published as US 2010-0057016 on Mar. 4, 2010, which Office Action is dated Oct. 24, 2013, and claims as pending for U.S. Appl. No. 12/198,947 as of Oct. 24, 2013.
Office Action for U.S. Appl. No. 12/864,293, filed Dec. 9, 2010, published as US 2011-0098635 on Apr. 28, 2011, which Office Action is dated Aug. 20, 2013, and claims as pending for U.S. Appl. No. 12/864,293 as of Aug. 20, 2013.
Office Action for U.S. Appl. No. 12/864,293, filed Dec. 9, 2010, published as US 2011-0098635 on Apr. 28, 2011, which Office Action is dated Jul. 7, 2014, and claims as pending for U.S. Appl. No. 12/864,293 as of Jul. 7, 2014.
Notice of Allowance for U.S. Appl. No. 12/864,293, filed Dec. 9, 2010, published as US 2011-0098635 on Apr. 28, 2011, which Notice of Allowance is dated Jan. 5, 2015, and claims as allowed for U.S. Appl. No. 12/864,293 as of Jan. 5, 2015.
Office Action for U.S. Appl. No. 14/522,761, filed Oct. 24, 2014, published as US 2015-0057603 on Feb. 26, 2015, which Office Action is dated Apr. 10, 2015, and claims as pending for U.S. Appl. No. 14/522,761 as of Apr. 10, 2015.
Office Action for JP Application No. 2013-236123 filed Nov. 14, 2013, which Office Action is dated Sep. 16, 2014, and claims as pending for JP Application No. 2013-236123 as of Sep. 16, 2014.
Office Action for CA Application No. 2713028 filed Jul. 22, 2010, which Office Action is dated Jan. 27, 2015, and claims as pending for CA Application No. 2713028 as of Jan. 27, 2015.
Examination Report for EP Application No. 09703486.2 filed Jan. 23, 2009, published as EP 2254615 on Dec. 1, 2010, which Examination Report is dated May 4, 2012, and claims as pending for EP Application No. 09703486.2 as of May 4, 2012.
Response to Communication dated May 4, 2012 for EP Application No. 09703486.2 filed Jan. 23, 2009, which Response is dated Nov. 14, 2012, and claims as pending for EP Application No. 09703486.2 as of Nov. 14, 2012.
Extended European Search Report for EP Application No. 16151482.3 filed Jan. 15, 2016, which Extended Search Report is dated Apr. 28, 2016, and claims as pending for EP Application No. 16151482.3 as of Apr. 28, 2016.
Office Action for MX Application No. MX/A/2010/008011 filed Jan. 23, 2009, which Office Action is dated Aug. 27, 2013, and claims as pending for MX Application No. MX/A/2010/008011 as of Aug. 27, 2013.
Invitation to Pay Additional Fees for International Application No. PCT/US2009/000433 (published as WO 2009/094179), dated Jun. 4, 2009.
International Search Report and Written Opinion for International Application No. PCT/US2009/000433 (published as WO 2009/094179), dated Sep. 25, 2009.
International Preliminary Report on Patentability for Application No. PCT/US2009/000433 dated Aug. 5, 2010.
Bengtsson et al., Haemo dialysis software architecture design experiences. Proceedings of the 1999 International Conference on Software Engineering. ACM New York, NY. 1999:516-525.
Choppy et al., Architectural patterns for problem frames. IEE Proceedings: Software. Aug. 2005;152(4):190-208.
Gentilini et al., Multitasked closed-loop control in anesthesia. IEEE Eng Med Biol Mag. Jan.-Feb. 2001;20(1):39-53.
Harel, Statecharts: A visual formalism for complex systems. Science of Computer Programming. 1987;8:231-274.
Krasner et al., A cookbook for using the model-view-controller user interface paradigm in smalltalk-80. JOOP. Aug. 1988;1(3):26-49.
Therakos, Inc., The Uvar® XTS™ System sales brochure, printed and handed out to customers and potential customers in Europe more than one year before the filing date of the instant application.

\* cited by examiner

FLEXIBLE TUBING OCCLUSION ASSEMBLY

RELATED APPLICATIONS

This application is a division of U.S. patent application Ser. No. 15/181,234, filed Jun. 13, 2016, and issued on Jul. 11, 2017, as U.S. Pat. No. 9,700,711, which is a division of U.S. patent application Ser. No. 13/480,236, filed May 24, 2012, and issued on Jun. 14, 2016, as U.S. Pat. No. 9,364,655, all of which are incorporated herein by reference in their entireties.

FIELD

The present specification generally describes occluder devices for occluding flexible tubing, particularly in medical infusion systems.

BACKGROUND

Medical devices, such as hemodialysis machines, medical infusion pumps, plasmapheresis devices, and the like, often require the use of tubing to facilitate the flow of fluids, e.g., to or from a patient using such device. Such tubing in many instances is made of a flexible material and is designed to be collapsible in order to facilitate peristaltic pumping and/or occlusion of fluid flow via collapse of the lumen of the flexible tubing. A variety of tubing clamps and tubing occlusion devices are known. Certain of these devices can be integrated into a medical infusion device and automatically controlled. In certain applications, medical infusion devices must handle fluids that include ingredients that, due to leakage or other factors that may lead to presence of the fluid on the external surfaces of the tubing, can become sticky and or result in fouling or failure of certain conventional tubing occluder designs.

SUMMARY

Described herein are occlusion assemblies configured to facilitate the opening and closing by occlusion of flexible tubing. In particular embodiments, the occlusion assemblies are associated with or form part of a medical infusion device, such as a hemodialysis device, peritoneal dialysis device, plasmapheresis device, etc., and may be controllably and automatically operated to facilitate fluid handling by such devices. The occlusion assemblies may be designed to position and immobilized the tubing and may include a frame or other support feature providing tubing guides and/or configured for attachment to or integration with a fluid handling assembly of a device of which they are part or with which they are used. The occlusion assemblies comprise a tubing occluder, which may be a mechanism constructed and positioned to apply a force to the tube(s) associated with the occlusion assembly to occlude the tubes and to release the force to allow the tubes to open for fluid flow. The occlusion assemblies and tubing occluders may be configured to include a single tube in certain cases, and in other cases to occlude multiple tubes, whether an odd number of tubes or an even number of tubes. Certain occlusion assemblies are specifically configured for occluding one or more pairs of tubes and may include tubing occluders having a separate occluding member for occluding each of the pair of collapsible tubes. The occlusion assemblies may include automatic actuators for operating the tubing occluders, and in certain cases also include a manual actuator to provide an override function. The occlusion assemblies may include a door designed and positioned to cover at least a portion of the tubes to be occluded and tubing occluder mechanism. Such occlusion assemblies may include safety features, for example, to prevent a release of occlusion force on the tubing when the door is not in a closed position and/or convenience features, for example a retainer mechanism to hold the tube occluder in a non-occluding position when the door is open with the tube occluder in the non-occluding position.

In one aspect, a variety of occlusion assemblies for occluding at least one collapsible tube of a medical infusion device are described. In certain embodiments, the occlusion assembly is configured for occluding at least one pair of collapsible tubes and comprises, for each pair of collapsible tubes, a first occluding member and a second occluding member, the first occluding member positioned adjacent to a first collapsible tube of the pair and the second occluding member positioned adjacent to a second collapsible to the pair, when the tubes are installed in the occlusion assembly for operation. The first occluding member and the second occluding member are further positioned adjacent from each other such that a space is defined between them. These space is on an opposite side of each occluding member then is the collapsible tube to which it is adjacent. The occlusion assembly further comprises a spreader positioned within the space between the occluding members and movable from a first position to a second position, wherein movement from the first position to the second position causes the spreader to force at least a portion of the first and second occluding members to move apart from each other to increase the size of the space between them and forced a tube-contacting portion of each occluding member against the collapsible tube to which it is adjacent to occlude the collapsible tube. The occlusion assembly further comprises at least one actuator constructed and positioned to move the spreader between the first and second positions.

In certain embodiments the occlusion assembly is configured for occluding at least one collapsible tube and comprises a frame comprising a tubing guide configured for positioning the collapsible tube, a tubing occluder mounted to the frame and comprising an occluding member constructed and positioned to controllably occlude or release occlusion of the collapsible tube, a door hingeably mounted to the frame and positioned to cover at least a portion of the collapsible tube and tubing occluder when in a closed position and to provide user access to the collapsible tube when in an open position, and a switch configured and positioned to detect when the door is in a closed position and to permit operation of the tubing occluder to release occlusion of the collapsible tube only when the door is in the closed position.

In certain embodiments and occlusion assembly for collapsing at least one collapsible tube comprises a tubing occluder comprising an occluding member constructed and positioned to controllably occlude or release occlusion of the collapsible tube, and automatic actuator operatively coupled to the tubing occluder to cause essentially linear motion of at least a portion of the tubing occluder to cause the occluding member to move from an occluding position to a non-occluding position, and an override mechanism operatively coupled to the tubing occluder to cause essentially linear motion of at least a portion of the tubing occluder to cause the occluding member to move from an occluding position to a non-occluding position upon manual operation of the override mechanism by a user.

In certain embodiments, and occlusion assembly for occluding at least one collapsible tube comprises a frame comprising a tubing guide configured for positioning the collapsible tube, a tubing occluder mounted to the frame and comprising an occluding member constructed and positioned to controllably occlude or release occlusion of the collapsible tube, a door hindgeably mounted to the frame and positioned to cover at least a portion of the collapsible tube and tubing occluder when in a closed position and to provide user access to the collapsible tube when in an open position, and a retainer mechanism engaged by the door when the door is in the closed position and configured to permit operation of the tubing occluder to occlude or release occlusion of the collapsible tube when the door is in the closed position and configured to engage and retain the tubing occluder in a non-occluding configuration when the door is opened while the tubing occluder is positioned in the non-occluding configuration.

In another aspect a method of operating an occlusion assembly for occluding at least one pair of collapsible tubes of a medical infusion devices disclosed. In one embodiment, the method involves moving a spreader of the occlusion assembly from a first position to a second position, wherein the spreader is positioned within a space defined between a first occluding member and a second occluding member to cause the spreader to force at least a portion of the first and second occluding members to move apart from each other to increase the size of the space between them and force a tube-contacting portion of each occluding member against a collapsible tube to which it is adjacent to occlude the collapsible tube.

Other advantages and novel features of the present invention will become apparent from the following detailed description of various non-limiting embodiments when considered in conjunction with the accompanying figures. In cases where the present specification and a document incorporated by reference include conflicting and/or inconsistent disclosure, the present specification shall control.

BRIEF DESCRIPTION OF THE DRAWINGS

The accompanying drawings are schematic are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings.

DETAILED DESCRIPTION

In accordance with one aspect of the disclosed invention, an occlusion assembly for compressing at least one flexible tube, for example a pair of flexible tubes is described. The occlusion assembly includes a tube occluder comprising a mechanism configured to occlude fluid flow within one or more flexible tubes, and in certain embodiments one or more pairs of flexible tubes. In certain embodiments, the tube occluder of the occlusion assembly comprises at least one occluding member, and in a specific embodiment comprises an occluding member for each section of tubing placed within the assembly. In certain such embodiments, each occluding member is pressed or otherwise forced or urged into an occluding position by an element that slides along a side of the occluding member, causing the occluding member to pivot at its proximal end and to translate toward the tubing at its distal end. In an embodiment, the element is positioned between two occluding members and acts to spread the distal ends of the occluding members away from each other as they press against their respective tubes. In a preferred option, a main spring urges the spreading element toward the distal ends of the occluding elements into an occluding position. The spreading element may be moved against the biasing force of the main spring into a non-occluding position near the proximal ends of the occluding elements either manually through a button and linkage assembly coupled to the spreading element, or by control of a controller activating an actuator that is also coupled to the spreading element. A hinged door may be configured to cover the occluding elements and their respective sections of tubing. Activation of the actuator may be prevented if the door is not properly closed over the occluding elements. Optionally, a retention element to hold the spreading element in a non-occluding position may be enabled when the door is in an open position. Enabling the retention element allows the spreader to be held in a non-occluding position without continued application of force by a user on the button or by continued activation of the actuator. The retention element may be disabled when the door is closed, so that the spreading element may be free to be moved into and out of an occluding position, either manually or via the actuator.

Figure 1:
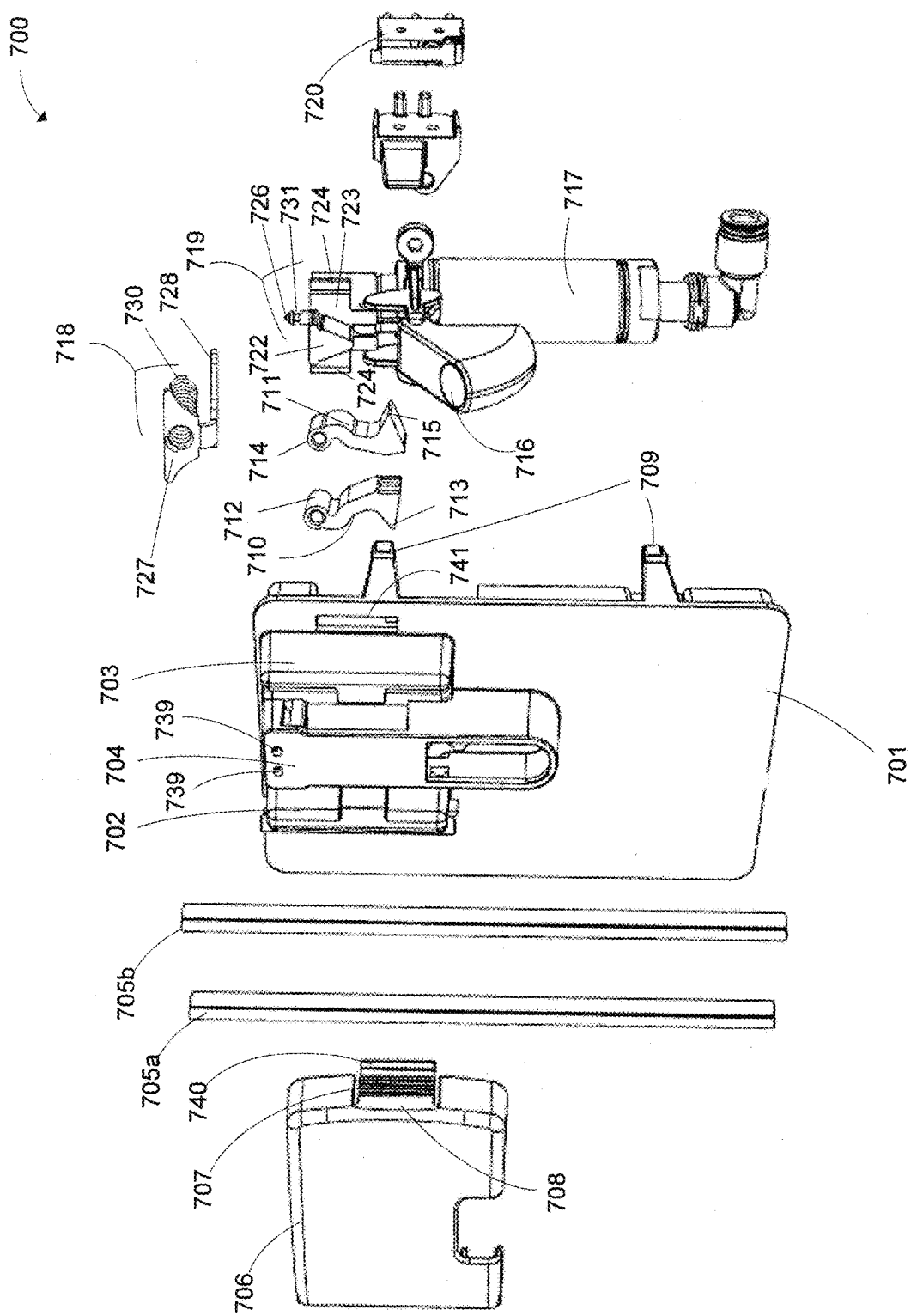
FIG. 1 shows an exploded, perspective view of an occlusion assembly from a front angle in accordance with an embodiment of the present disclosure.
Figure 2:
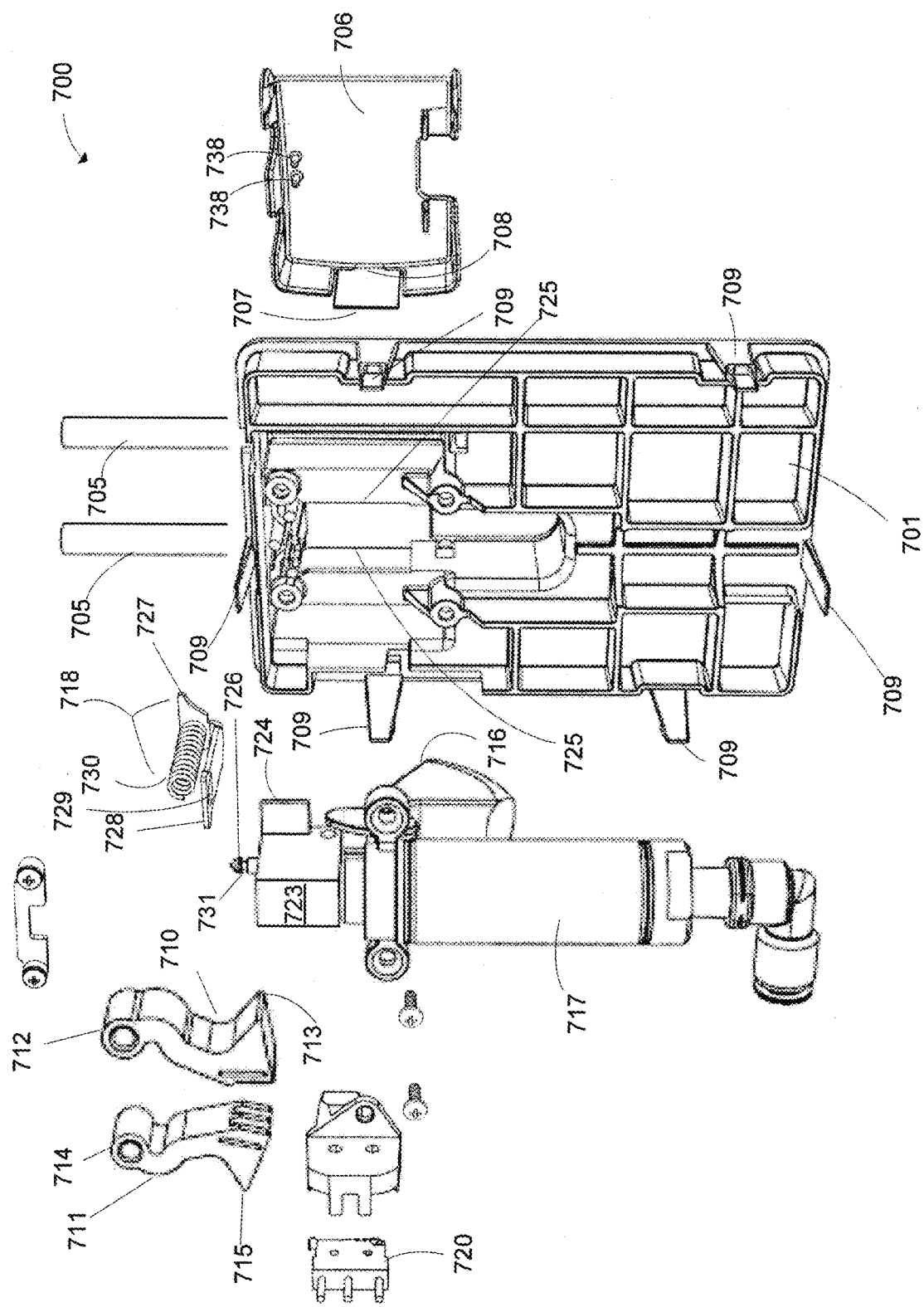
FIG. 2 shows an exploded, perspective view of the occlusion assembly of FIG. 1 from a back angle.

FIGS. 1 and 2 show exploded, perspective views of an occlusion assembly 700 in accordance with an embodiment of the present disclosure. FIG. 1 shows an exploded, perspective view of the occlusion assembly 700 from a front angle and FIG. 2 shows an exploded, perspective view of the occlusion assembly 700 from a back angle.

The occlusion assembly 700 receives a pair of tubes 705 and is configured to occlude the tubes 705 using a pinching action at approximately the same level along the length of assembly 700. The pinching action reduces the size of an inner fluid pathway of each tube 705 to restrict the flow of fluid therethrough. The occlusion assembly 700 may be used with an infusion pump, in a dialysis machine, in hemodialysis, in peritoneal dialysis, in hemofiltration, in hemodiafiltration, in intestinal dialysis, and the like.

The occlusion assembly 700 includes a frame 701. In some embodiments, the frame 701 includes tabs or snaps 709 for securing the frame to corresponding slots on a front panel of a blood filtration device, such as a hemodialysis apparatus.

Figure 3:
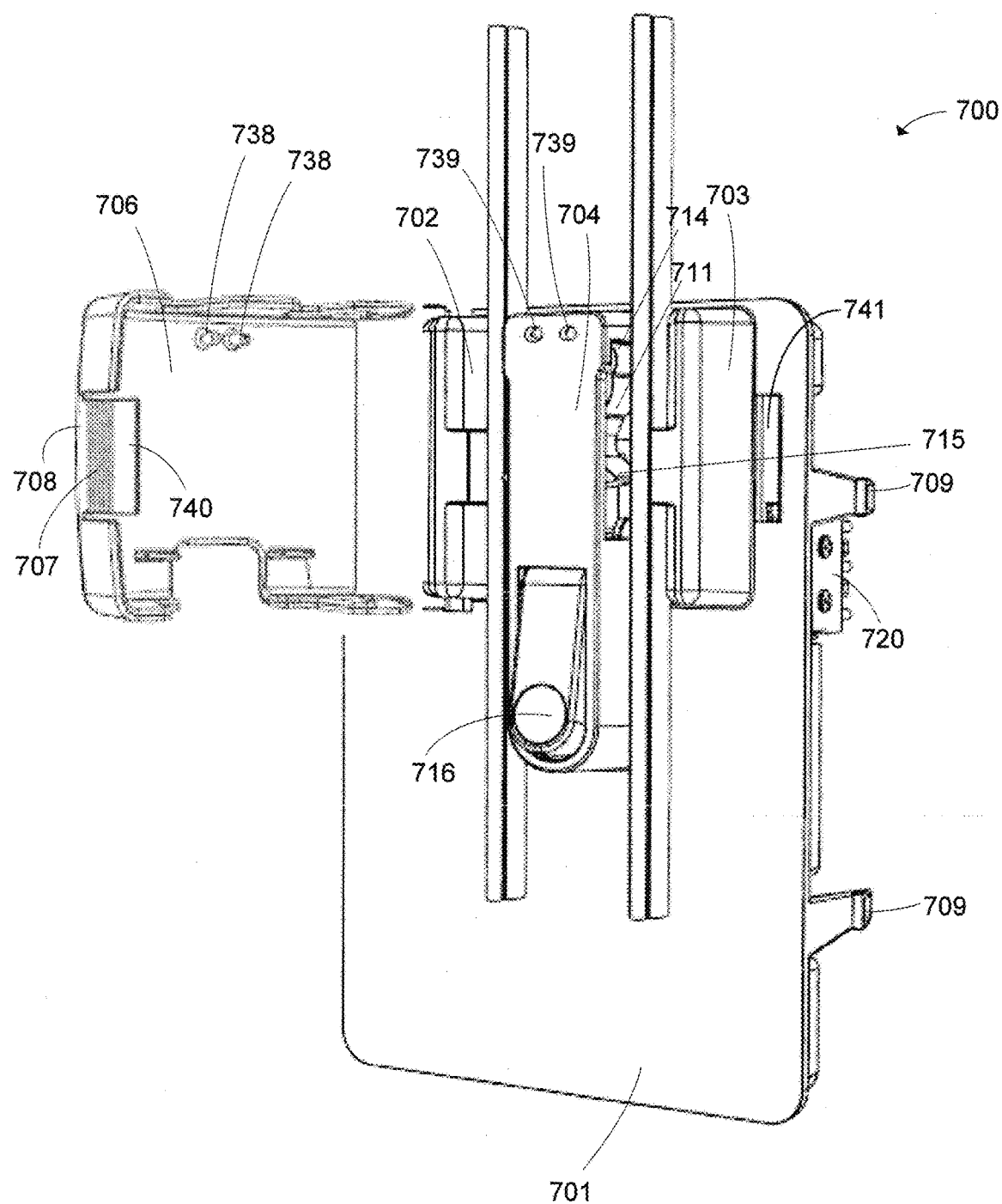
FIG. 3 shows a front, perspective view of the occlusion assembly of FIG. 1 with the door open and the button pressed to illustrate loading of a tube.
Figure 4:
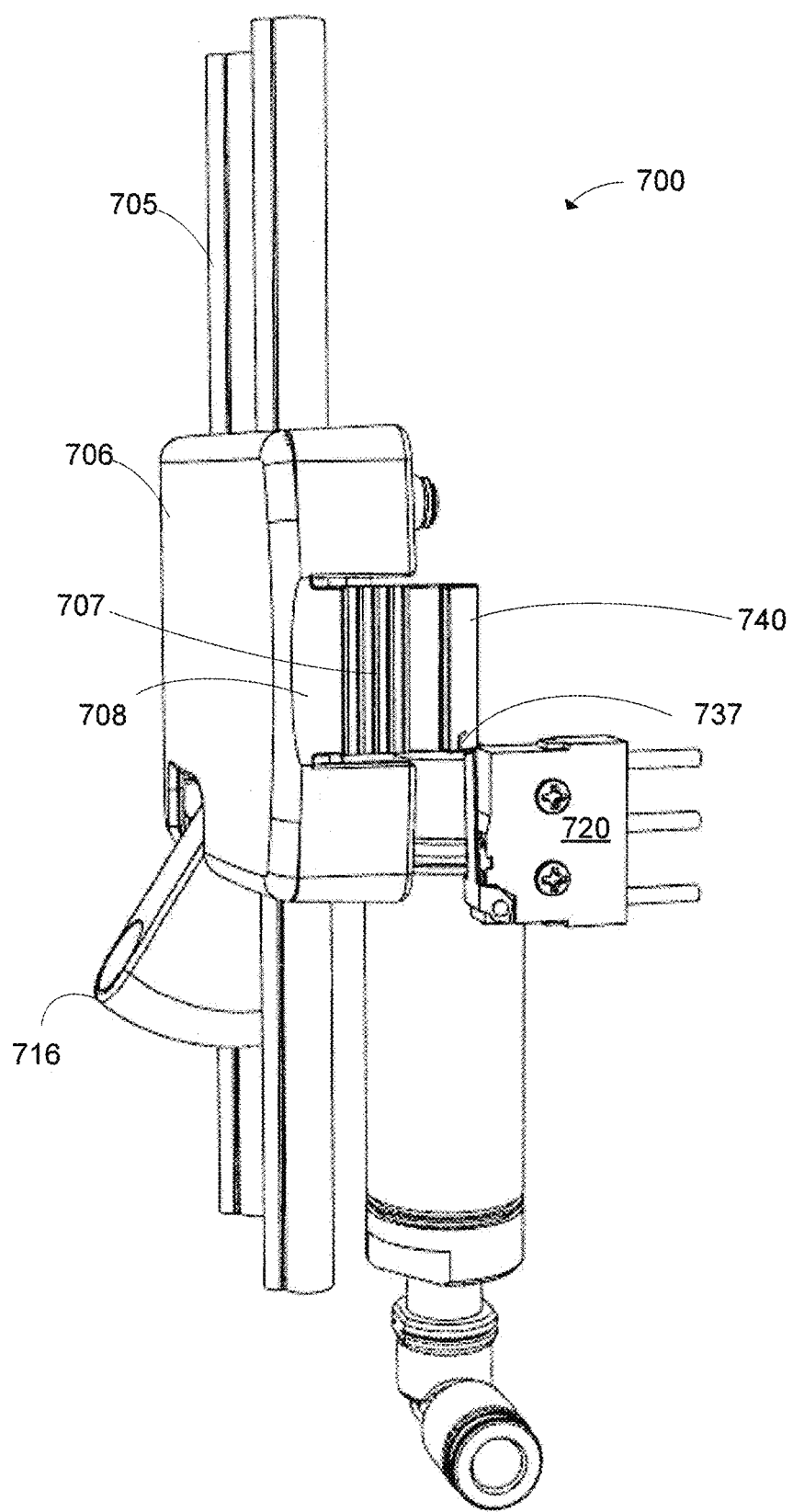
FIG. 4 shows a close-up perspective view of the occlusion assembly of FIG. 1, showing the door engaging a switch when the door is closed.

The frame 701 includes anvils or blocks 702 and 703 against which a tube 705 is compressed by the occluding ends 713 of a pair of occluding arms 710 and 711, and a tube guide 704 to position each tube 705 against blocks 702 and 703. The tube guide 704 and blocks 702 and 703 are configured to each position a tube 705 in a predetermined position adjacent to each of the blocks 702 and 703. The occlusion assembly 700 also includes a door 706 which is pivotally mounted to the frame 701. The door 706 can shut against the frame 701 to secure the tubes 705 between each of the blocks 702 and 703 and the tube guide 704. The door 706 includes a latch 707, which may be co-molded with or otherwise attached to the door 706 via a hinge, such as for example a resilient, flexible base portion (e.g., via a living hinge) 708 to secure the door 706 to the frame 701 in a closed position. As shown in FIGS. 1, 3, and 4, a latch 707 may be pressed laterally to release a catch 740 from engagement with a corresponding slot 741 on frame 701 to open the door 706.

Figure 5:
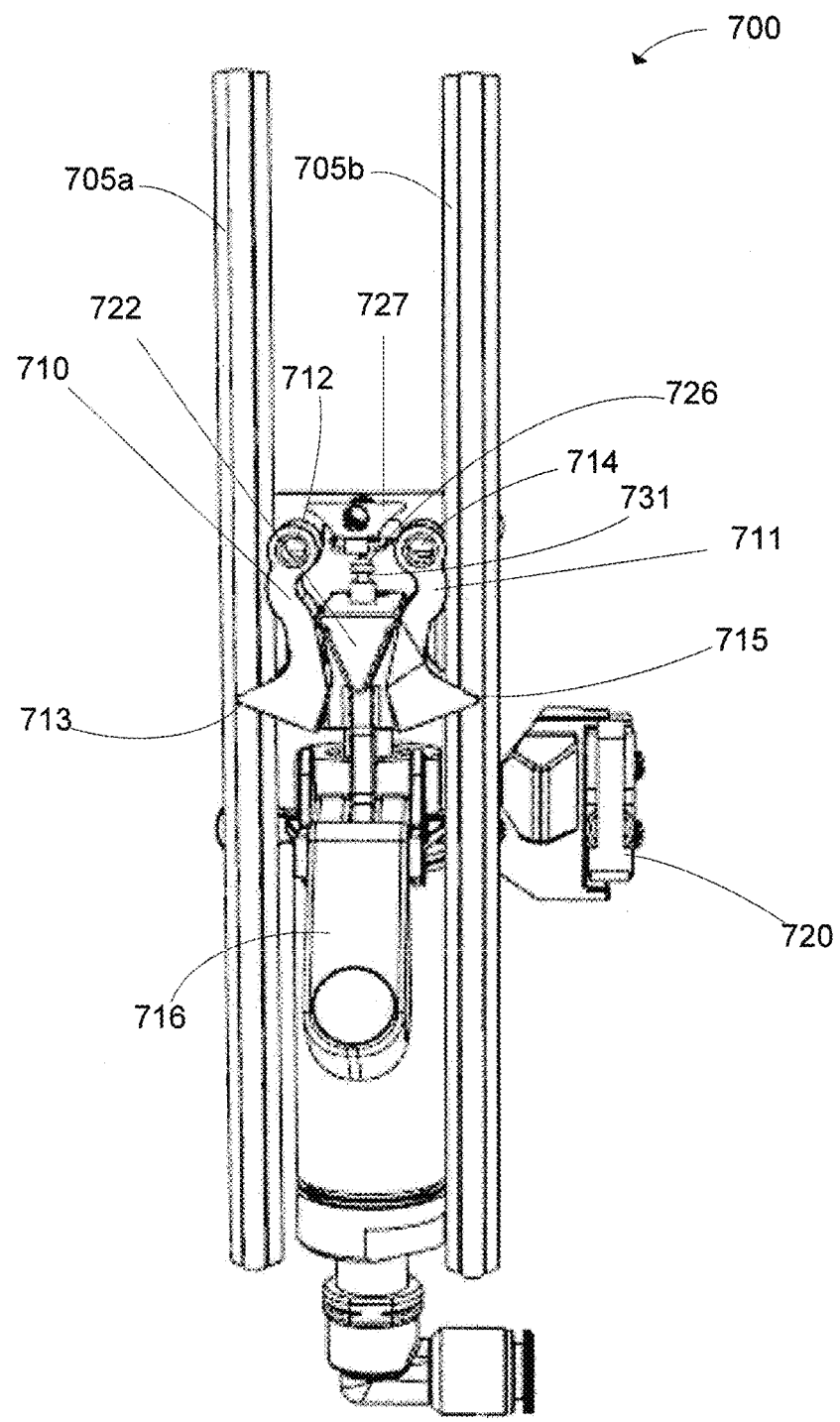
FIG. 5 shows the front of the occlusion assembly of FIG. 1 without the door and frame to illustrate the arms fully occluding flexible tubes.

The occlusion assembly 700 includes two arms 710 and 711. The first arm 710 includes a pivoting end 712 and an occluding end 713; likewise, the second arm 711 includes a pivoting end 714 and an occluding end 715. The two arms 710 and 711 operate together to occlude the tubes 705 when a manual actuator, such as button 716, is released (or in other embodiments engaged) and door 706 is closed, or when an actuator 717 is deactivated FIG. 3 shows a front, perspective view of the occlusion assembly 700 with the door 706 open and the button 716 pressed to illustrate release of occluding arms 710 and 711 to permit loading and unloading of the tubes 705 in accordance with an embodiment of the present disclosure. FIG. 5 shows the front of the occlusion assembly 700 of FIG. 1 without the door 706 and frame 701 to illustrate the arms 710 and 711 fully occluding the tubes 705a, b in accordance with an embodiment of the present disclosure. As shown in FIG. 5, a wedge element or spreader 722 contacts the facing sides of occluding arms 710 and 711, which under spring force can apply pressure to occluding arms 710 and 711 to press the occluding ends 713 and 715 of occluding arms 710 and 711 against a portion of tubes 705a, b. A user may release the occluding arms 710 and 711 by pressing button 716, which causes spreader 722 to withdraw away from occluding arms 710 and 711, releasing the pressure of spreader 722 being applied to the distal ends of occluding arms 710 and 711. In some aspects, the manual actuator (e.g. button 716) acts as an override mechanism to an automated actuator (such as, for example, a pneumatically operated piston/cylinder apparatus) connected to a tubing occluder element (e.g., the spreader 722). The manual actuator is operatively coupled to the tubing occluder to cause essentially linear motion of at least a portion of the tubing occluder, moving the occluding member from an occluding position to a non-occluding position upon manual operation of the override mechanism by a user.

Similarly, activation of an actuator may release occluding arms 710 and 711 by causing spreader 722 to withdraw away from the occluding ends 713, 715 of occluding arms 710 and 714. In one embodiment, as shown in FIG. 1, spreader 722 may be formed of, co-molded with, attached to or connected to a carriage assembly 723, which in turn is connected to an actuating arm of the actuator (see, e.g., FIGS. 7-9). The actuator may comprise, for example, a motor and gear assembly (e.g., rack and pinion assembly or worm-type gear assembly), a solenoid, a hydraulic cylinder or a pneumatic cylinder, among others. In a preferred embodiment, the actuator comprises a pneumatic cylinder 717 that causes an actuating arm comprising a piston arm 742 to extend linearly against a spring force (which in an embodiment may be a coil spring 745 within cylinder 717 as shown in FIG. 11). As shown in FIG. 11, in a perspective side view of a pneumatically operated linear actuator 717, piston arm 742 is connected to carriage 723. When activated by pneumatic pressure, actuator 717 extends piston arm 742 and moves carriage 723 and attached spreader 722 in a direction that withdraws spreader 722 from engagement with the distal ends 713, 715 of the occluding arms 710 and 711. (For clarity, occluding arm 711, frame 701, door 706, block 703 and tube guide 704, among other elements, have been removed from FIGS. 9-11). Preferably, a main spring that is either external or internal to cylinder/actuator 717 may apply a biasing force to piston arm 742 or carriage 723 to cause spreader 722 to move occluding arms 710 and 711 to an occluding position. In the event of a loss of power or pneumatic pressure, the occluding arms 710 and 711 will default to an occluding mode, preventing the flow of fluid through tubes 705. As illustrated in a cross-sectional view of occlusion assembly 700 in FIG. 11, in an embodiment, a coil spring 745 may be placed within the cylinder 743 to provide a biasing force against which piston 744 may move piston arm 742 under pneumatic pressure. Pneumatic pressure may be supplied to linear actuator 717 from a pressure source (e.g., a tank pressurized by a pump) regulated by an intervening electromechanical valve under control of an electronic controller.

Figure 10:
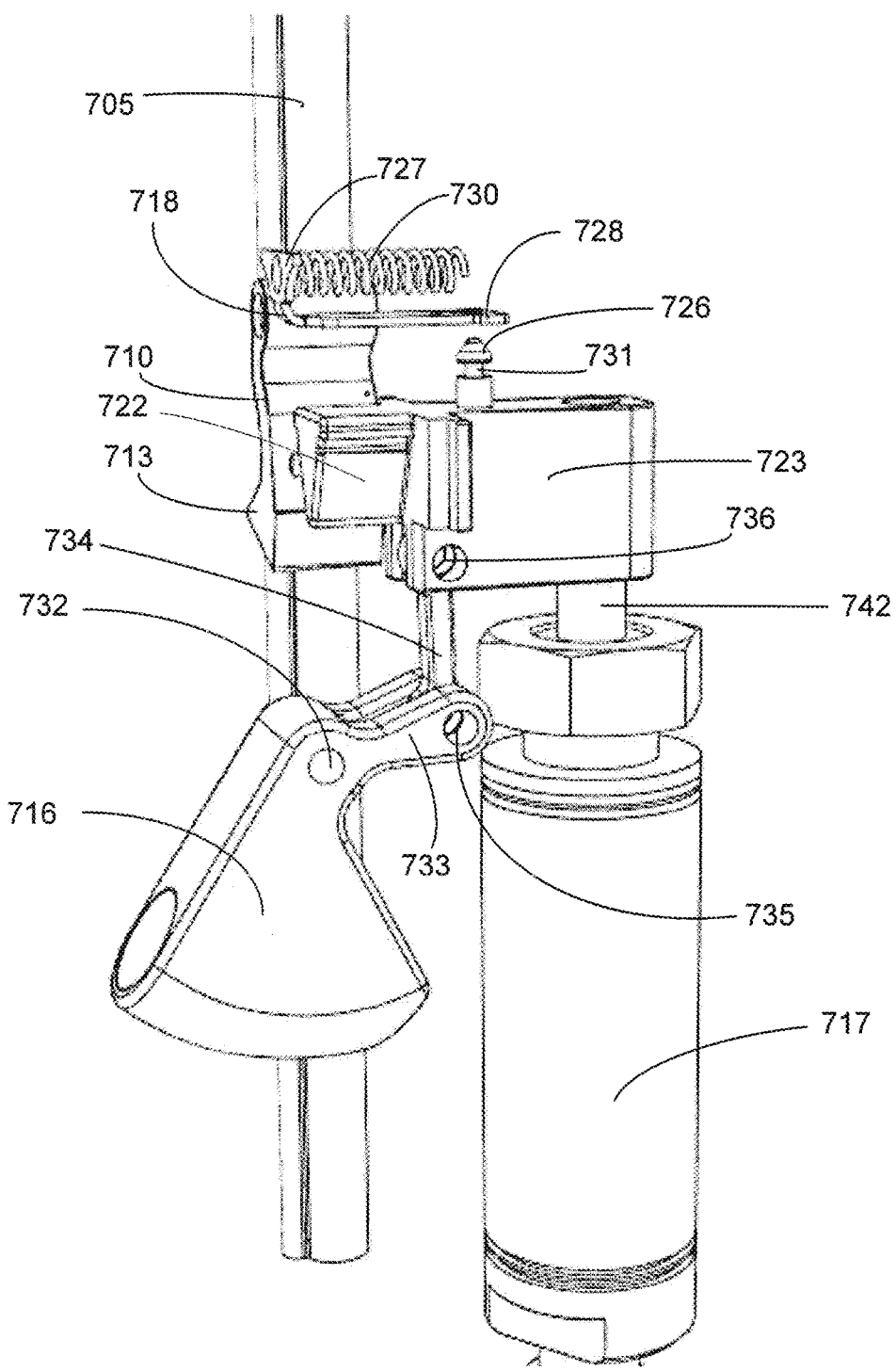
FIG. 10 shows a side perspective view of several working parts of the occlusion assembly of FIG. 1 in an occluding state.
Figure 11:
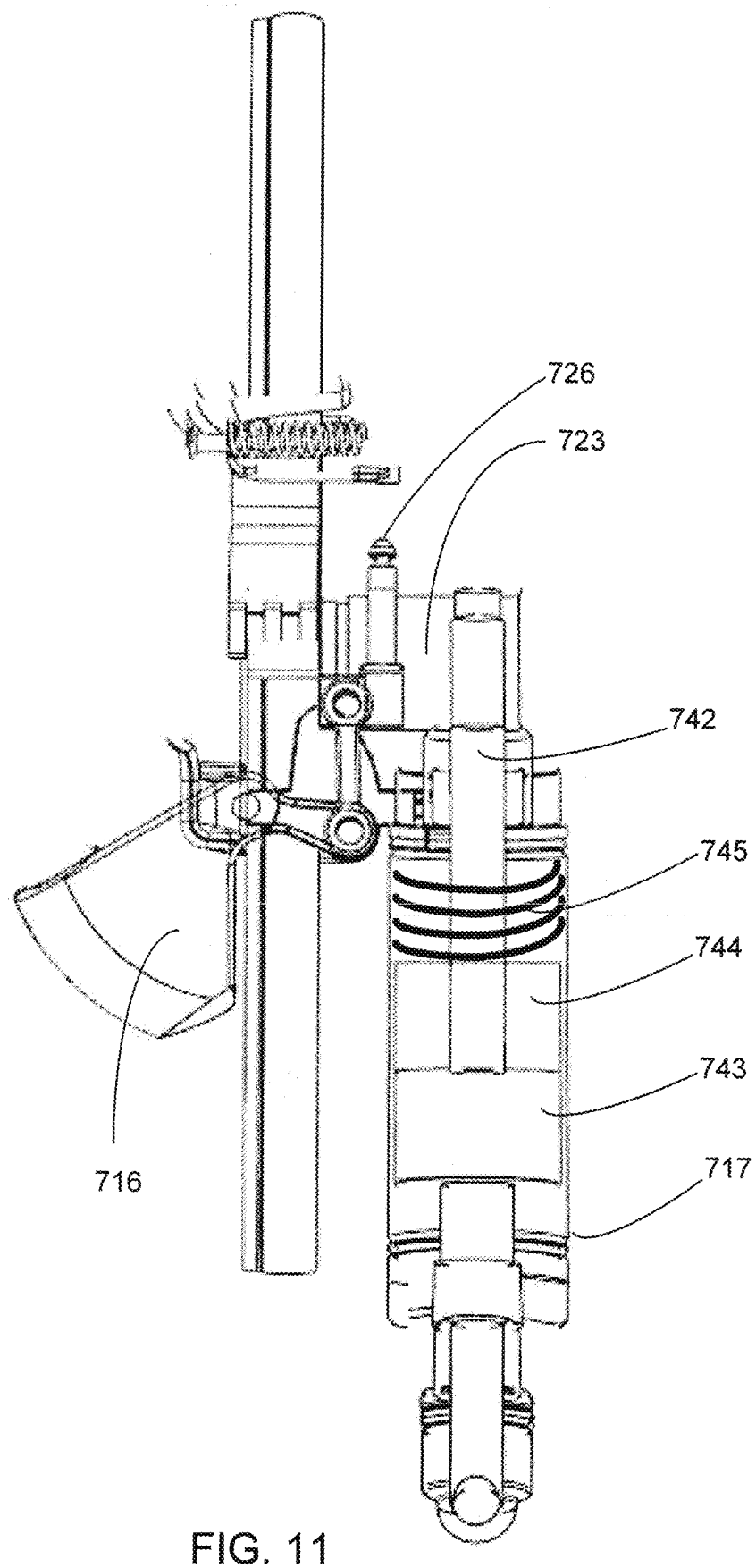
FIG. 11 shows a side, cross-sectional view of an actuator of the occlusion assembly of FIG. 1, illustrating a location for a main spring for the assembly.

As shown in FIGS. 5 and 10, when the linear actuator 717 is fully retracted, the carriage 723 carries spreader 722 along the facing sides of the occluder arms 710 and 711 to rotate them into an occluding position. The first arm 710 pivots about its pivoting end 712 to cause the occluding end 713 to press against first tube 705a that is restrained by block 702 (see FIG. 5). The second arm 711 pivots about its pivoting end 714 such that the occluding end 715 can press against second tube 705b which is restrained by block 703.

Figure 6:
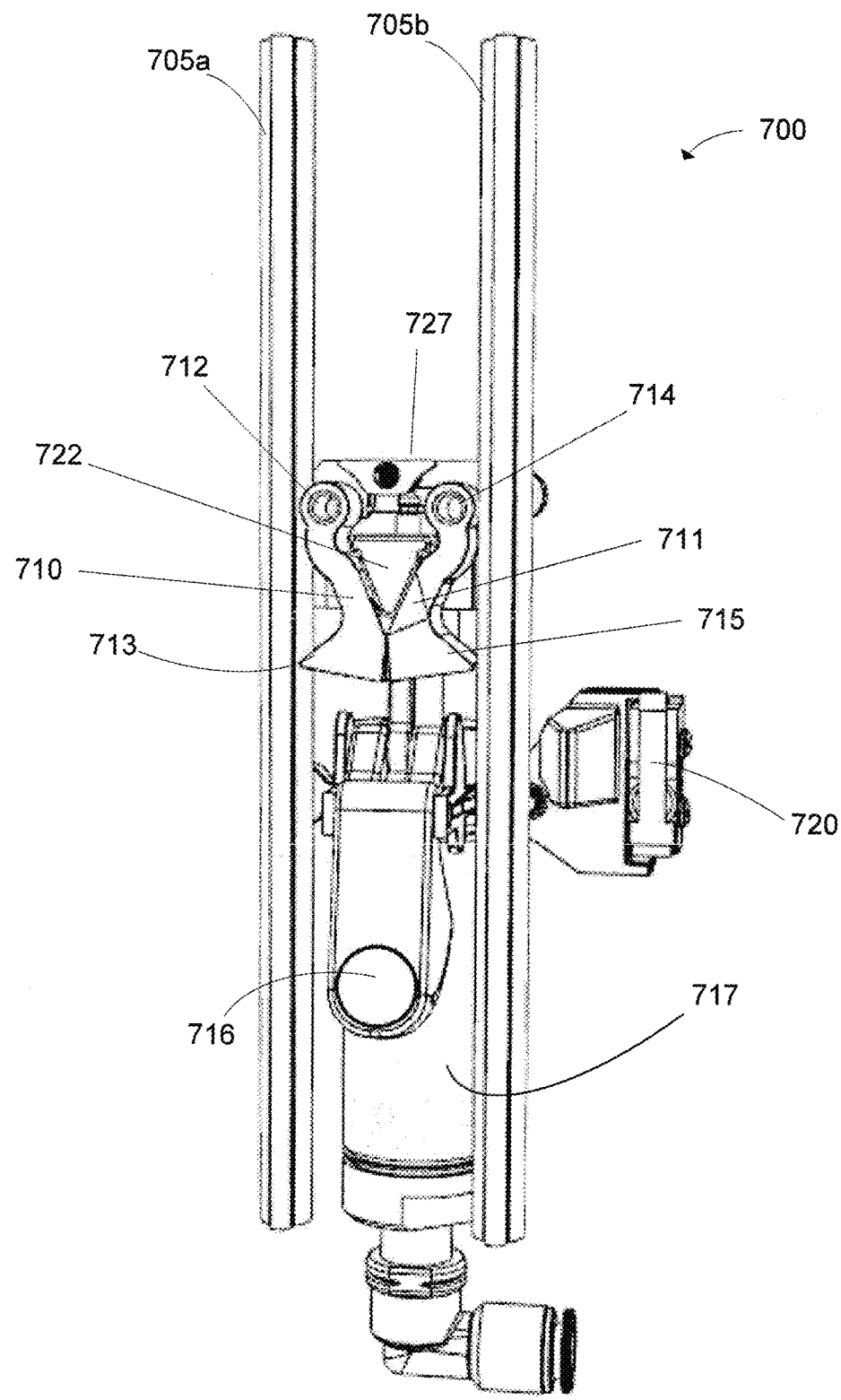
FIG. 6 shows the front of the occlusion assembly of FIG. 1 without the door and frame to illustrate the arms in a non-occluding position.
Figure 9:
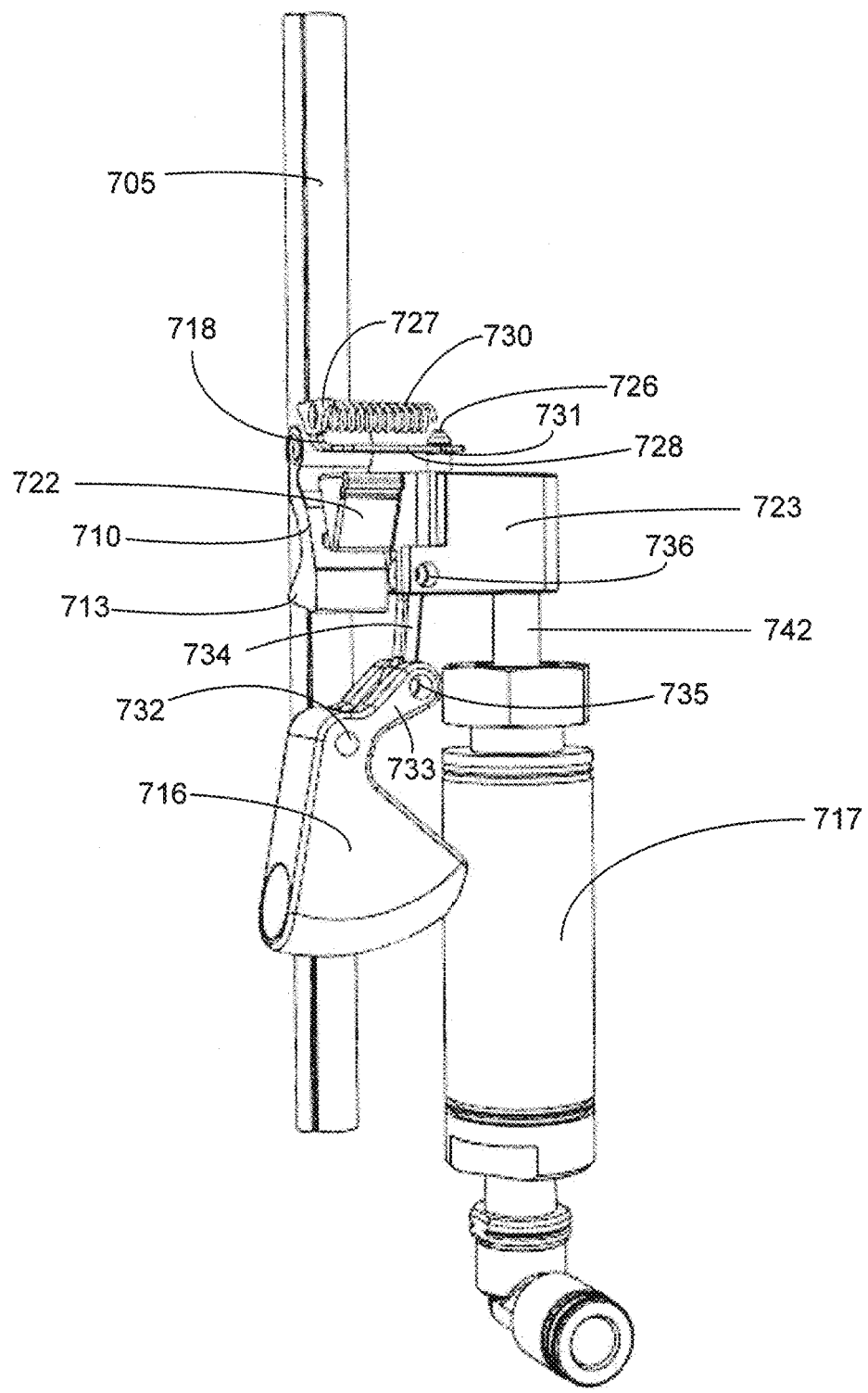
FIG. 9 shows a side perspective view of several working parts of the occlusion assembly of FIG. 1 in a non-occluding state.

FIGS. 6 and 9 show occlusion assembly 700 in a non-occluding state (frame 701, door 706, blocks 702, 703, and other elements removed for clarity). When the button 716 is pressed or the linear actuator 717 is activated, the carriage 723 and attached spreader 722 move distally away from the actuator 717, allowing occluder arms 710 and 711 to rotate about pivot points 712 and 714 into a non-occluding position. The elastic resilience of the tubes 705a.b may cause the arms 710 and 711 to pivot towards each other. In some embodiments of the present disclosure, small magnets (not explicitly shown) embedded in the arms 710 and 711 pull the arms 710 and 711 towards each other to facilitate the retraction of the occluding ends 713 and 715 away from the tubes 705. In other embodiments, small springs (not shown)

may bias occluding arms 710 and 711 to pivot toward each other, the spring constants being weak enough to be overcome by the main spring (e.g., spring 745) biasing carriage 723 or spreader 722 into retracted (occluding) positions.

FIG. 4 shows a perspective side view of the occlusion assembly 700 of FIG. 1 (frame 701 removed for clarity) showing the door 706 engaging a switch 720 when the door 706 is closed in accordance with an embodiment of the present disclosure. As shown in FIG. 4, the hinge portion 708 of latch 707 is coupled to an engagement member or catch 740 that can snap into a cooperating slot 741 of the frame 701 (see, e.g., FIGS. 1 and 3). As the door 706 is closed, a portion of the catch 740 of latch 707 of the door 706 engages a spring-loaded switch 720, which in an embodiment includes a spring arm 737 of the switch 720.

Engagement of switch 720 by closure of door 706 signals an electronic controller (not shown) that the door 706 is properly closed, and that linear actuator 717 may be activated to release occluders 710 and 711 to allow fluid to flow through tubes 705. The door 706 closure signal may also cause the controller to perform other functions, such as, for example, instructing a pump coupled to the tubes 705 to begin pumping fluid within tubes 705.

Figure 7:
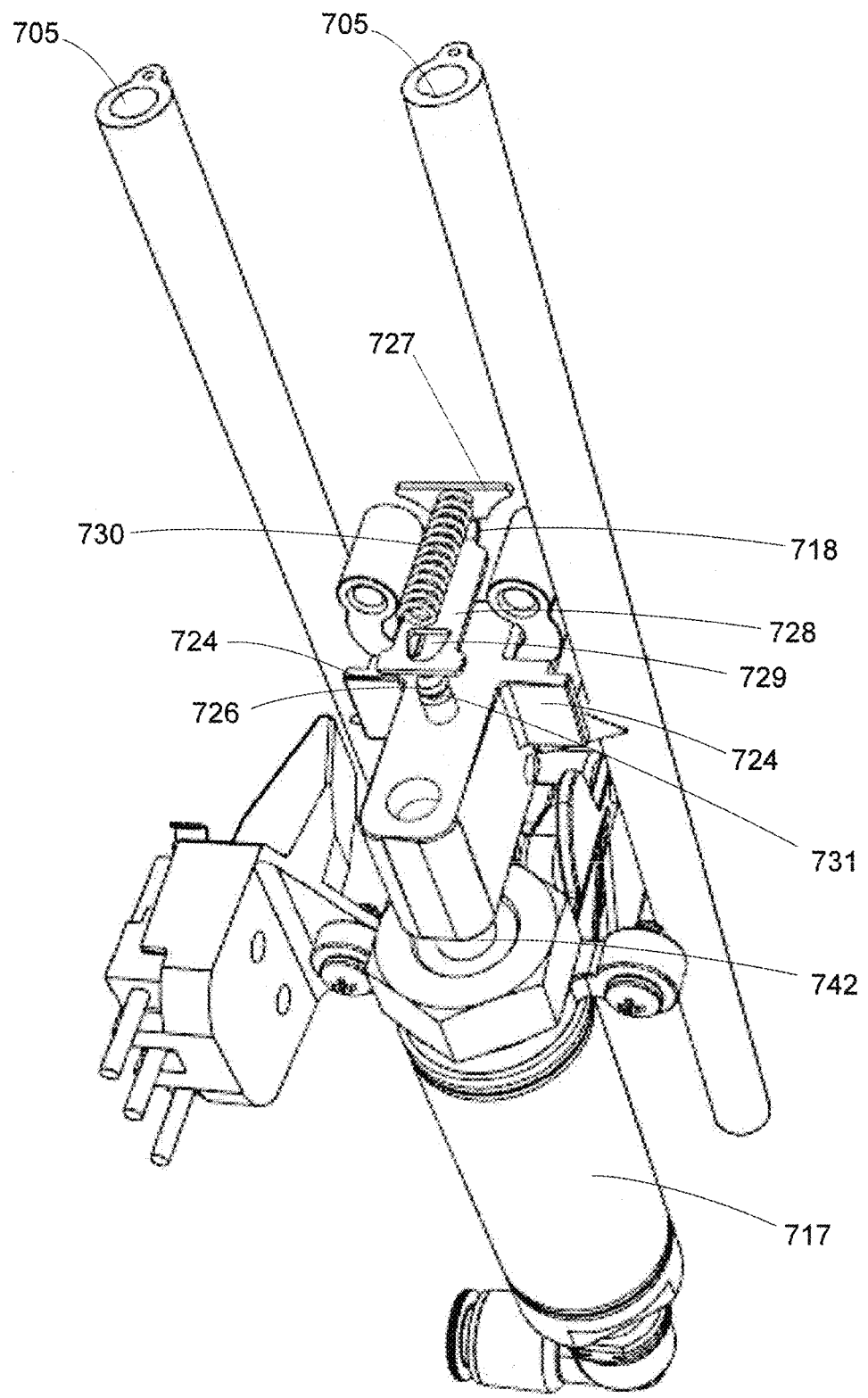
FIG. 7 is a rear/top perspective view of the occlusion assembly of FIG. 1 with an actuator arm in a fully retracted position.

FIG. 7 shows the back of the occlusion assembly 700 of FIG. 1 with the linear actuator 717 in a fully retracted position (i.e., in the occluding position) in accordance with an embodiment of the present disclosure. FIG. 7 shows the back side of the occlusion assembly 700 in the same configuration as shown for the front view of occlusion assembly 700 in FIG. 5. FIG. 7 shows several working parts of the occlusion assembly 700 of FIG. 1 to illustrate the operation of the actuator 717 and carriage 723 in accordance with an embodiment of the present disclosure. The carriage 723 moves with the extension or retraction of the piston arm 742 or with the actuation of the button 716. The carriage 723 includes guides 724 attached to or co-molded with the carriage 723. The guides 724 guide the carriage 723 as it moves via actuation of the piston arm 742 or with the actuation of the button 716. The guides 724 interface with tracks 725 of the frame 701 (see, e.g., FIG. 2).

In an optional embodiment, when door 706 is open, actuation of button 716 by a user or activation of actuator 717 by a controller causes carriage 723 and spreader 722 to move into a non-occluding position, and a retaining element or assembly allows the non-occluding position to be held without further force being applied either by the user or by the actuator 717. In an exemplary embodiment shown in FIG. 7, the carriage 723 may incorporate a latching pin 726 to cooperate with a slot or hole in a retention member 718. The retention member 718 includes a surface 727 positioned to be contacted by pins 738 located on the inside of door 706 when it is closed (see, e.g., FIGS. 2 and 3). Through holes 739 (see, e.g. FIGS. 1 and 3) allow pins 738 to contact a portion of retention member 718 to displace it in a rearward direction. In the illustrated embodiment, pins 738 contact front plate 727 of retention member 718. Retention member 718 also includes a surface having a slot or hole 729 positioned to receive the head of a latching pin 726, which in the illustrated embodiment comprises a horizontal plate 728 defining a receiving portion 729. Retention member 718 is arranged to slide within grooves or guides of the frame 701 (not shown) in response to contact by the pins 738 when the door 706 is closed or opened (see, e.g. FIG. 2). A spring 730 mounted on the frame 701 may be biased to urge the retention member 718 forward to a stop feature (not shown) on the frame 701 so that opening the door 706 allows the retention member 718 to slide forward, re-aligning the receiving portion 729 in relation to the latching pin 726. When the door 706 is closed (see FIG. 1 or 2), the pins 738 on the door 706 press against the front plate 727 which compresses the spring 730 such that the receiving portion 729 of the horizontal plate 728 is positioned directly over the latching pin 726. Upon alignment of the receiving portion 729 with the latching pin 726, the area of the receiving portion 729 is large enough to allow the latching pin 726 to be released by the retention member 718, thereby allowing the carriage 723 to be subject to the spring force of the main spring 745 in the actuator 717. If pneumatic pressure is not then being applied to the actuator 717, the carriage 723 is then free to move into an occluding position. The retention member 718 in the disabled state (i.e., inoperative state) allows the latching pin 726 to move freely through the receiving portion 729 as the carriage 723 moves between the fully extended position and the fully retracted position.

Figure 8:
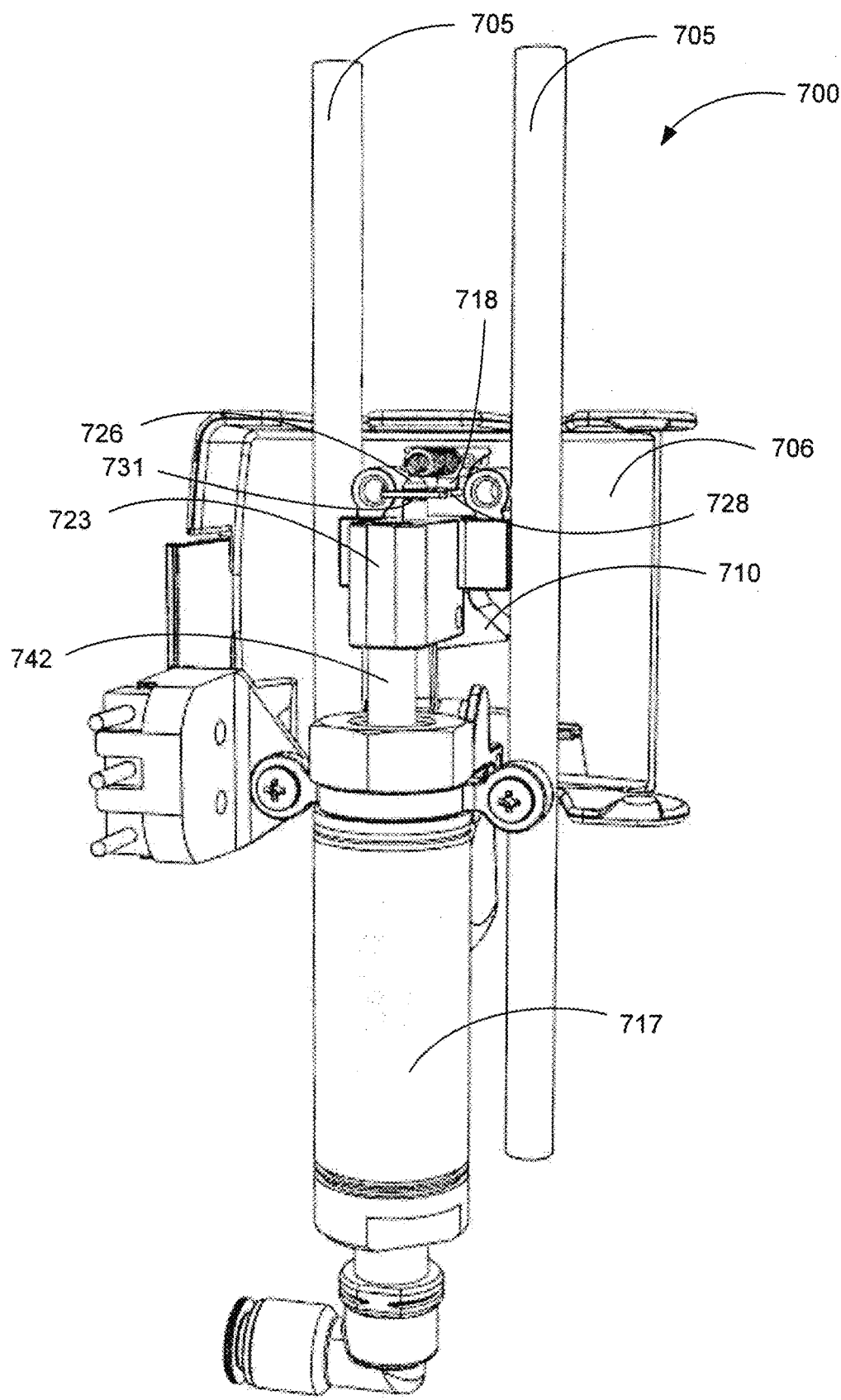
FIG. 8 is a rear perspective view of the occlusion assembly of FIG. 1 with an actuator arm in a fully extended position.

FIG. 8 is a rear view of the occlusion assembly 700 with the actuator 717 activated, and the piston arm 742 in an extended position to place the occluding arms 710, 711 in a non-occluding state. In this view, the head of the latching pin 726 is noted to be above the plane of the horizontal plate 728 of the retention member 718, and the recessed region 731 of the latching pin 726 is noted to be aligned with the receiving portion 729 of the retention member 718. In this illustration, door 706 is in a closed position, implying that the receiving portion 729 is in a sufficiently rearward position to prevent the latching pin 726 from being latched into the retention member 718.

When the door 706 is sufficiently opened, the pins 738 of the door 706 do not press against the front plate 727 and the spring 730 applies a force on the front plate 727 such that the receiving portion 729 of the retention member 718 is positioned to allow the latching pin 726 to engage an edge of the receiving portion 729 and latch to the retention member 718. The latching pin 726 moves into the receiving portion 729 pulling the front plate 727 rearward against the force of the spring 730 when the receiving portion 729 is positioned to latch to the latching pin 726. When the head of latching pin 726 moves sufficiently through the receiving portion 729, a recessed region 731 below the head of latching pin 726 becomes co-aligned with the horizontal plate 728 which moves as the edge of the receiving portion 729 moves into the recessed region 731 under the force of the spring 730 as applied to the front plate 727. When the pins 738 of the door 706 sufficiently engage the front plate 727, the receiving portion 729 is positioned to release the latching pin 726 from the latch 718. Thus, when the door 706 is open, the carriage 723 and spreader 722 can be held in a non-occluding position without the continuous application of force by the actuator 717 or by a user pressing against the button 716. This permits a user to load and unload tubing from occlusion assembly 700 without simultaneously having to apply force on the button 716. However, upon the closing of the door 706, the retention member 718 is no longer operative, and in the absence of continued application of force by either the actuator 717 or through the button 716, the carriage 723 and spreader 722 will move into a position to cause the occluding arms 710 and 711 to rotate to an occluding position.

FIGS. 9 and 10 show a side perspective view of several working parts of the occlusion assembly 700 of FIG. 1, with frame 701, blocks 702, 703, tube guide 704, door 706, occluding arm 711 and other parts removed for clarity. In FIG. 9, the piston arm 742 is fully extended in accordance with an embodiment of the present disclosure. FIG. 9 shows the latching pin 726 latched onto the retention member 718. That is, assuming that door 706 is in an open position, the horizontal plate 728 is positioned by the force of spring 730 to engage the recessed region 731 of the latching pin 726.

FIG. 10 shows a side, perspective view of the occlusion assembly 700 of FIG. 1 with the piston arm 742 in a fully retracted position, with certain elements removed as in FIG. 9 for clarity. In this example, the latching pin 726 is shown to be completely disengaged from the retention member 718; and in the absence of an activating force on the actuator 717 or a pressing force on the button 716, the piston arm 742, carriage 723 and spreader 722 are free to retract under the force of a main spring 745 (see FIG. 11) biased against the extension of piston arm 742. The spreader 722 then moves toward the occluding ends 713, 715 of the occluding arms 710, 711. In an embodiment, as shown in FIGS. 9 and 10, the button 716 pivots about a pivot 732 to raise a lever arm 733 when the button 716 is pressed. The lever arm 733 is pivotally connected to a connecting member 734 via a proximal pivot 735. The connecting member 734 in turn is pivotally connected to the carriage 723 via a distal pivot 736. When the button 716 is pressed or the piston arm 742 moves the carriage 723 toward the retention member 718, the connecting member 734 moves with the carriage 723, rotating the button 716 about the pivot 732 as shown in FIG. 9.

Figure 12:
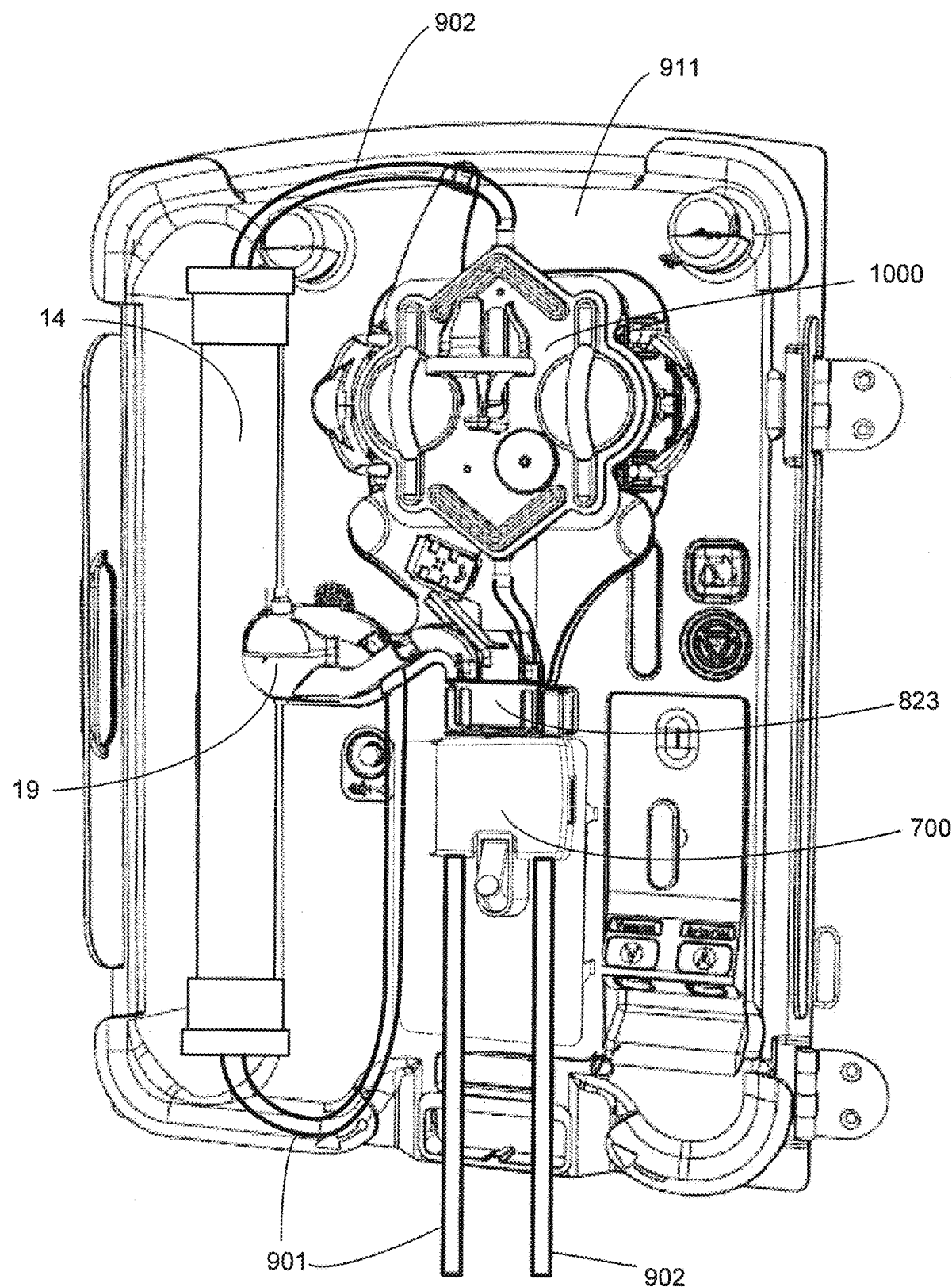
FIG. 12 shows the occlusion assembly of FIG. 1 mounted in a front panel assembly of a hemodialysis apparatus in accordance with an embodiment of the present disclosure.

FIG. 12 shows the occlusion assembly 700 of FIG. 1 used in a front-panel assembly 911 of a dialysis system in accordance with an embodiment of the present disclosure. The occlusion assembly 700 occludes flexible tubes 901, 902 through which blood flows to and from a patient. The right side tube 902 carries blood from a patient into a blood pump assembly 1000 and the left side tube 901 carries blood from a dialyzer 14 back to the patient after passing through an air trap 19. The occlusion assembly 700 can occlude the flow of blood through both of these patient tubes 801, 802 simultaneously.

The tubes 901, 902 are connected to a blood pump cassette or assembly 1000. The blood pump cassette 1000 is a modular unit that may be mounted onto and dismounted from the front-panel assembly 911. Both of the patient tubes 901, 902 may be provided as an assembly with the blood pump cassette 1000 and air trap 19, and may be loaded into the occlusion assembly 700 when the blood-pump cassette 1000 is mounted onto the front-panel assembly 911. In this embodiment, the occlusion assembly 700 forms a permanent part of the front panel assembly 911.

When the occlusion assembly 700 is in the non-occluding state, pumps located on blood pump cassette 1000 may be activated to pump blood from a patient through the right tube 902, up through the blood pumps and through a dialyzer 14. Blood processed by the dialyzer 14 then returns to the patient via tube 901 after first passing through an air trap 19 and an air-in-line detector 823.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention.

What is claimed:

1. An occlusion assembly for occluding at least one collapsible tube of a medical infusion device, comprising:
    a frame comprising a tubing guide configured for positioning the at least one collapsible tube;
    a tubing occluder mounted to the frame and comprising an occluding member constructed and positioned to controllably occlude or release occlusion of the at least one collapsible tube;
    a door hingeably mounted to the frame and positioned to cover at least a portion of the at least one collapsible tube and the tubing occluder when in a closed position and to provide user access to the at least one collapsible tube when in an open position; and
    a retaining member engaged by the door when the door is in the closed position and configured to allow operation of the tubing occluder to occlude or release occlusion of the at least one collapsible tube when engaged by the door in the closed position, and configured to hold the tubing occluder in a non-occluding position when the door is moved from the closed position to the open position while the tubing occluder is in the non-occluding position.

2. The occlusion assembly of claim 1, wherein the tubing occluder comprises a carriage assembly slidably mounted to the frame, and wherein the carriage assembly
    i. is operatively coupled to an actuator that is configured to cause sliding motion of the carriage assembly,
    ii. is operatively coupled to an occluding member engaging element configured to move the occluding member into an occluding position or permit the occluding member to move into the non-occluding position upon sliding motion of the carriage assembly, and
    iii. comprises a latching pin.

3. The occlusion assembly of claim 2, wherein the retaining member is movably mounted to the frame, the retaining member comprising a surface configured and positioned to be engaged by a portion of the door when the door is in the closed position, the retaining member further comprising a latching pin receiving hole sized and positioned to allow substantially unrestricted entry of the latching pin into the latching pin receiving hole upon sliding motion of the carriage assembly in a direction to permit the occluding member to move into the non-occluding position and exit of the latching pin from the latching pin receiving hole upon sliding motion of the carriage assembly in a direction to move the occluding member into the occluding position when the door is in the closed position, wherein the retaining member is biased for movement upon opening of the door to cause the latching pin receiving hole to move into engaging and retaining contact with the latching pin when the carriage assembly is positioned to place the occluding member in its non-occluding position when the door is in the open position.

4. The occlusion assembly of claim 1, wherein the door comprises one or more contact elements on a portion of the door facing the retaining member when the door is in the closed position, and wherein the retaining member comprises a contact surface arranged to interact with the one or more contact elements of the door when the door is moved from the open position to the closed position.

5. The occlusion assembly of claim 4, wherein the retaining member comprises a retainer spring biased to apply a force against the contact surface of the retaining member, and against the door via the one or more contact elements when the door is in the closed position.

6. The occlusion assembly of claim 5, wherein the retaining member is configured to move to a non-retaining position when the door is moved to the closed position and to move to a retaining position under force of the retainer spring when the door is moved to the open position.

7. The occlusion assembly of claim 6, wherein the tubing occluder comprises a latching pin with a head portion and a narrower neck portion, and the retaining member comprises a longitudinal plate defining a slot, the head portion of the latching pin configured to be captured by the slot of the retaining member when the door is in the open position and the tubing occluder is moved from an occluding position to the non-occluding position.

8. The occlusion assembly of claim 7, wherein the retaining member comprises a face plate perpendicular to the longitudinal plate, and wherein the retainer spring is positioned to apply a force against the face plate, wherein the slot of the retaining member includes a receiving portion sufficiently wide to receive the head portion of the latching pin and comprises a retaining portion narrower than the receiving portion and configured to receive the neck portion of the latching pin, and wherein the receiving portion is aligned with the latching pin when the door is in the closed position, and the retaining portion is aligned with the latching pin when the door is in the open position.

9. The occlusion assembly of claim 8, further comprising a manual actuator configured for operation by a user, the manual actuator arranged to move the tubing occluder to the non-occluding position and to move the latching pin through the receiving portion of the retaining member when the door is in the closed position, wherein opening the door while the user operates the manual actuator causes the head portion of the latching pin to be captured by the slot of the retaining member, allowing the tubing occluder to remain in the non-occluding position after release of the manual actuator by the user.

10. The occlusion assembly of claim 9, wherein the manual actuator comprises a push button adjacent the door and operable by the user when the door is in the closed position.

11. The occlusion assembly of claim 9, comprising a pneumatic actuator coupled to the tubing occluder, the pneumatic actuator coupled to an actuator spring biased to place the tubing occluder in the occluding position when the pneumatic actuator is not actuated, wherein actuation of the pneumatic actuator places the tubing occluder in the non-occluding position.

12. The occlusion assembly of claim 11, wherein the manual actuator and the actuator spring are arranged to allow the user to manually override a biasing force of the actuator spring to place the tubing occluder in the non-occluding position.

13. The occlusion assembly of claim 1, further comprising:
at least one actuator operatively coupled to the tubing occluder to cause the occluding member of the tubing occluder to move from an occluding position to the non-occluding position.

14. The occlusion assembly of claim 13, wherein the at least one collapsible tube comprises a first collapsible tube and a second collapsible tube, wherein the occluding member of the tubing occluder is a first occluding member and the tubing occluder further comprises a second occluding member, wherein the occlusion assembly is configured for occluding the first collapsible tube and the second collapsible tube, and wherein the tubing occluder is constructed and positioned with respect to the first collapsible tube and the second collapsible tube so that:
the first occluding member is positioned adjacent to the first collapsible tube, and the second occluding member is positioned adjacent to the second collapsible tube, when the first collapsible tube and the second collapsible tube are installed in the occlusion assembly for operation; and so that
the first occluding member and the second occluding member are further positioned adjacent to each other such that a space is defined between the first occluding member and the second occluding member, the space being on a side of the first occluding member that is opposite to a side of the first occluding member that is adjacent to the first collapsible tube, and the space being on a side of the second occluding member that is opposite to a side of the second occluding member that is adjacent to the second collapsible tube; and wherein the occlusion assembly further comprises:
a spreader positioned within the space and movable within the space from a first position to a second position, wherein movement from the first position to the second position causes the spreader to force at least a portion of the first and second occluding members to move apart from each other to increase size of the space and to force a tube-contacting portion of each occluding member against the the respective first or second collapsible tube to which it is adjacent.

15. The occlusion assembly of claim 14, wherein the spreader is wedge shaped and coupled to the at least one actuator, and wherein the at least one actuator causes the spreader to move in an essentially linear path from the first position to the second position to engage with the first and second occluding members and move them apart from each other.

16. The occlusion assembly of claim 15, wherein the first occluding member comprises a first occluder arm and the second occluding member comprises a second occluder arm, with each of the first occluder arm and the second occluder arm having a proximal end pivotally mounted to the frame and a distal end comprising a tube contacting surface, and wherein movement of the spreader by the at least one actuator causes each of the first occluder arm and the second occluder arm to pivot such that the tube contacting surface of the first occluder arm moves apart from the tube contacting surface of the second occluder arm such that each tube contacting surface compresses and occludes the respective first or second collapsible tube to which it is adjacent.

17. The occlusion assembly of claim 16, wherein the occlusion assembly is configured so that the first collapsible tube and the second collapsible tube are occluded in an absence of a force applied by the at least one actuator to cause release of occlusion.

18. The occlusion assembly of claim 17, wherein the at least one actuator comprises a biasing element configured to provide a restoring force causing occlusion of the first collapsible tube and the second collapsible tube in an absence of positive actuation of the at least one actuator to overcome the restoring force and release occlusion of the first collapsible tube and the second collapsible tube.

19. The occlusion assembly of claim 13, wherein the at least one actuator is pneumatically powered.

20. The occlusion assembly of claim 1, wherein the occlusion assembly comprises a portion of a fluid handling assembly of a dialysis system.

21. The occlusion assembly of claim 1, wherein the occlusion assembly further comprises at least one collapsible tube mounted thereto.

* * * * *